United States Patent [19]

Sano et al.

[11] 3,930,948

[45] Jan. 6, 1976

[54] ENZYMATIC METHOD FOR PRODUCING AROMATIC ETHYLAMINES

[75] Inventors: Konosuke Sano, Machidi; Keizo Matsuda, Kawasaki; Hidetsugu Nakazawa, Uji; Koji Mitsugi, Yokohama, all of Japan

[73] Assignee: Ajinomoto Co., Inc., Tokyo, Japan

[22] Filed: July 29, 1974

[21] Appl. No.: 492,906

[30] Foreign Application Priority Data
Aug. 3, 1973  Japan.................................. 48-87399

[52] U.S. Cl..................................... 195/29; 195/66
[51] Int. Cl.²......................................... C12D 13/00
[58] Field of Search................................ 195/29, 66

[56] References Cited
UNITED STATES PATENTS
3,579,427   5/1971   Nakayama et al.................... 195/29

OTHER PUBLICATIONS

Methods in Enzymology, Vol. XVII, Part B, pp. 652–656, (1971).

*Primary Examiner*—Alvin E. Tanenholtz
*Attorney, Agent, or Firm*—Hans Berman; Kurt Kelman

[57] ABSTRACT

A decarboxylase in cells of Micrococcus strains converts tryptophan, phenylalanine, and substitution products thereof to the corresponding phenyl- and indolylethylamines. The enzyme can be recovered in pure state from the microorganisms, but cells and cell material are effective enzyme sources in the decarboxylation reaction.

3 Claims, 1 Drawing Figure

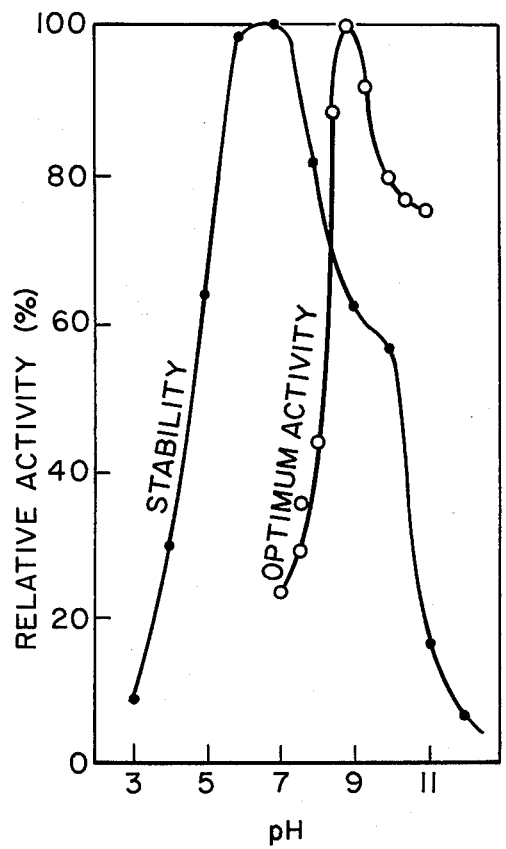

ENZYMATIC METHOD FOR PRODUCING AROMATIC ETHYLAMINES

This invention relates to an enzymatic method for producing aromatic ethylamines, and more particularly to a method for producing arylethylamines from the corresponding amino acids by decarboxylase.

Arylethylamines such as tryptamine, serotonine and 3,4-hydroxyphenylethylamine are used in medicine. It is known that animal tissues contain a small amount of decarboxylase active for aryl amino acids. Decarboxylase separated from animal tissues is expensive.

It has now been found that certain microorganisms of genus Micrococcus produce larger amount of decarboxylase active for aryl amino acids. Various arylethylamines can be produced at a lower cost using the newly found bacterial decarboxylase.

The sole FIGURE of the appended drawing diagrammatically illustrates the effect of pH on stability and activity of a decarboxylase of the invention.

Arylethyl amines, may be produced by holding aryl amino acids and an effective amount of decarboxylase in an aqueous solution at pH 5 to 12 at a temperature of 10° to 50°C, and recovering the arylethylamines produced in the aqueous solution.

The decarboxylase of this invention can be isolated from cells of a microorganism belonging to genus Micrococcus by the following procedure.

A. PREPARATION OF PURIFIED DECARBOXYLASE

All phosphate buffer used in the following decarboxylase preparation process contained $5 \times 10^{-5}$ M pyridoxal phosphate, $10^{-2}$ M mercapto ethanol and $10^{-4}$ M EDTA, and all processes were carried out at 5°C, except as described below.

CULTIVATION

An aqueous culture medium was prepared to contain, per deciliter, 0.5 g yeast extract, 3 ml soyprotein-acid hydrolyzate ("AJIEKI"), 0.5 g peptone, 0.5 g glycerol, 0.1 g $KH_2PO_4$, 0.1 g $MgSO_4.7H_2O$, 1 mg $FeSO_4.7H_2O$, 1 mg $MnSO_4.7H_2O$, and was adjusted to pH 8.0 with KOH respective 45 liter batches of the aqueous medium were placed in 17 50 liter fermenters, inoculated with *Micro-coccus percitreus* AJ 1065 and cultured at 30°C for 20 hours. Cells were collected by centrifuging 760 l broth, and 10.5kg cell paste were obtained.

EXTRACTION OF ENZYME

The cell paste was suspended in 18 l of 0.05 M phosphate buffer (pH 7.0) and disrupted by "Dyno mill." After centrifuging, 22.46 l cell extract was obtained.

FIRST PROTAMINE PRECIPITATION

The cell extrace was mixed gradually with 292 g protamine sulfate suspended in 1 liter of 0.05 M phosphate buffer, and agitated for 1 hour. The precipitate formed was removed by centrifuging.

FIRST AMMONIUM SULFATE FRACTIONATION

Solid ammonium sulfate was added to 20.4 l cell extract treated with protamine to 30% saturation, and the precipitate formed was removed by centrifuging. Solid ammonium sulfate was added further to the supernatant to 50 percent saturation. After standing overnight, the precipitate was collected by centrifuging, and dissolved in 0.05 M phosphate buffer. The solution (10 l) was dialyzed for 24 hours against three changes of 15 l of 0.01 M phosphate buffer.

SECOND PROTAMINE PRECIPITATION

The dialyzed solution (1430 ml) was mixed with 10 g/dl protamine sulfate solution, and stirred for 1 hour. The precipitate formed was removed by centrifuging. The supernatant was dialyzed against three changes of 10 l of 0.01 M phosphate buffer.

DEAE-SEPHADEX COLUMN CHROMATOGRAPHY

The dialyzed enzyme solution (1420 ml) was subjected to DEAE-Sephadex column chromatography. DEAE-Sephadex A-50 was packed in a column (13 × 20 cm) and equlibrated with 0.05 M phosphate buffer. The enzyme solution was passed through the column, and then the column was washed with 0.1 M phosphate buffer.

Active fractions were combined, to the combined eluate was added solid ammonium sulfate to 50 percent saturation, and precipitated protein was collected by centrifuging. Ammonium sulfate was removed by dialysis against 0.01 M phosphate buffer.

HYDROXYLAPATITE COLUMN CHROMATOGRAPHY

The dialyzed enzyme solution (300 ml, containing 7.71 g protein) was subjected to hydroxylapatite column chromatography. Hydroxylapatite was packed in a column (4.5 × 5 cm), and equilibrated with 0.01 M phosphate buffer. The enzyme solution was passed through the column. The enzyme was eluted with 0.05 M phosphate buffer, and active fractions were collected and dialyzed against 0.05 M phosphate buffer.

SECOND AMMONIUM SULFATE FRACTIONATION

The dialyzed eluate was mixed with solid ammonium sulfate to 40 percent saturation, and the precipitate formed was collected. Ammonium sulfate was removed by dialysis.

THIRD AMMONIUM SULFATE FRACTIONATION

Ammonium sulfate fractionation was carried out again to 35 percent saturation, and ammonium sulfate was removed from the precipitate.

SECOND DEAE SEPHADEX CHROMATOGRAPHY

The enzyme solution (92 ml) was subjected to DEAE Sephadex column chromatography. DEAE Sephadex A-25 was packed in a column (4.4 × 14 cm), and equilibrated with 0.05 M phosphate buffer. The enzyme solution was passed through the column, subsequently eluted with potassium chloride solutions increasing in concentration at a linear gradient from 0.1 to 0.3 M in 0.1 M phosphate buffer.

Active fractions were collected in an amount of 690 ml, and protein was precipitated with ammonium sulfate.

FIRST SEPHADEX G-200 CHROMATOGRAPHY

The precipitated protein was dissolved in 3 ml of 0.05 M phosphate buffer, and passed through a Sephadex G-200 column (4.5 × 71 cm).

FOURTH AMMONIUM SULFATE FRACTIONATION

Protein precipitated by 30 – 45 percent saturation of ammonium sulfate was collected, and ammonium sulfate was removed by dialysis.

SECOND SEPHADEX G-200 CHROMATOGRAPHY

The enzyme solution was passed through a Sephadex G-200 column (2.5 × 90 cm). Protein was precipitated by 55 percent saturated ammonium sulfate solution. Ammonium sulfate was removed by dialysis.

CRYSTALLIZATION

Decarboxylase was crystallized from the dialyzed solution by gradually adding ammonium sulfate. This crystallization was repeated once more.

B. CRYSTALLINE DECARBOXYLASE

Purity: more than 95 percent
SDS-disc acrylamide gel electrophoresis: gave a single band
Sedimentation patterns: single symmetric peak in the ultra-centrifuge $S_{20w}^0$: 6.2 S
$D_{20w}$: 6.0 × $10^{-7}$ cm²/sec.
Molecular weight: 94,000
  (by sedimentation velocity)
Number of subunits: 2
  (by SDS electrophoresis)
Absorbance maxima: 280 nm ($E_{280}^{1\%} = 11.8$)
                   340 nm
                   415 nm
Optimum pH for activity: 9.0 (see attached drawing)
Km for L-tryptophan: 2.4 mM
V max for L-tryptophan: 21.7 units/mg
Required cofactor: pyridoxal phosphate (Km 22 $\mu$M)
Turnover number: 1.02 × $10^3$ $\mu$M/min/$\mu$M pyridoxal phosphate Microorganisms which produce aryl amino acid decarboxylase are, for example, Micrococcus percitreus AJ 1065 (FERM-P 2200), and Micrococcus conglomeratus AJ 1015 (FERM-P 2199).

The aqueous medium employed for culturing the microorganisms is entirely conventional, and contains assimilable sources of carbon and nitrogen, inorganic salts and minor organic nutrients. Assimilable carbon sources are, for example, glucose, sucrose, maltose, molasses, starch, starch hydrolyzate, acetic acid, citric acid and ethanol. Assimilable nitrogen sources are, for example, gaseous ammonia, aqueous ammonia, ammonium salts, nitrate salts and urea.

As the minor organic nutrients, amino acids, vitamins, peptone, bouillon, yeast extract, soyprotein-acid hydrolyzate, corn steep liquor are used. They serve also as nitrogen and carbon sources. Preferably tryptophan or phenylalanine is added to the aqueous medium to promote formation of the decarboxylase.

Cultivation is carried out for 1 to 5 days, preferably at pH 4 to 10, and at 25° to 40°C under aerobic conditions.

The broth may be used as an enzyme source as it is, without removing the bacterial cells. Washed cells, acetone-treated cells, freeze-dried cells, cell homogenate, or sonicate can also be used as the enzyme source.

The reaction mixture contains an aryl amino acid and the decarboxylase of this invention, and a minor amount of vitamin $B_6$. The mixture is desirably maintained at a temperature of 10° to 50°C, and at pH 5 to 12.

Amino acids decarboxylated by the enzyme of this invention are phenylalanine, tryptophan, and tyrosine, and derivatives thereof as shown in Examples below. The amount of the amino acids contained in the reaction mixture is usually 0.1 to 10 g/dl.

The arylethylamines produced in the reaction mixture are recovered by conventional methods such as extracting with organic solvents.

EXAMPLE 1

An aqueous culture medium was prepared to contain, per deciliter, 1 g yeast extract, 1 g peptone, 0.5 g KCl and 0.2 g L-tryptophan, and was adjusted to pH at 7.0 with KOH 0.50 ml batches of the medium were placed in 500 ml shaking flasks, and sterilized with steam. Micrococcus percitreus AJ 1065 was inoculated in the medium, and cultured at 30°C for 24 hours. Cells were separated from the cultivation broth by centrifuging, and freeze-dried.

a reaction mixture containing, per deciliter, 1 g L-tryptophan, 1 g $KH_2PO_4$, 0.01 g pyridoxal phosphate and 1 g freeze-dried cells and having a pH of 9.5 was maintained at 30°C for 40 hours. Thereafter cells were removed by centrifuging, and the supernatant was adjusted to pH 13.5. Tryptamine was extracted with 800 ml ethylalcohol. 3.1 G of tryptamine hydrochloride was obtained from 400 ml of reaction mixture.

Tryptamine was identified by paper chromtography, paper electrophoresis, NMR spectrum, infra-red spectrum, and ultraviolet spectrum.

EXAMPLE 2 an aqueous culture medium was prepared to contain per deciliter, 1 g yeast extract, 1 g peptone, 0.5 g KCl, 0.2 g 5-hydroxytryptophan, and adjusted to pH 7.0. 50 Ml batches of the medium were placed in 500 ml shaking flasks and sterilized with steam.

Micrococcus conglomeratus AJ 1015 was inoculated in the medium, cultured at 30°C for 24 hours, and cells were collected by centrifuging.

A reaction mixture containing per deciliter 5-hydroxytryptophan, 1 g $KH_2PO_4$, 0.01 g pyridoxal phosphate and 3 g wet cells, of pH 9.0 was prepared, and 200 ml of the mixture was incubated at 30°C for 48 hours.

The mixture was then adjusted with $Na_2CO_3$ to pH 10, and 120 g NaCl was added. Serotonine was extracted with 200 ml n-butanol, and 1.2 g serotonine hydrochloride were obtained from the butanol solution.

EXAMPLE 3

An aqueous culture medium was prepared to contain, per deciliter, 1 g yeast extract, 1 g peptone, 0.5 g KCl, and 0.2 g L-phenylalanine, and adjusted to pH 7.0. 50 Ml batches of the medium were placed in 500 ml shaking flasks, sterilized with steam, inoculated with freeze-dried cells of Micrococcus percitreus AJ 1065, and cultured aerobically at 30°C for 24 hours. The cells so obtained were freeze-dried.

A reaction mixture was prepared to contain per deciliter 1 g L-phenylalanine, 1 g $KH_2PO_4$, 0.01 g pyridoxal phosphate and 1 g freeze-dried cells, and adjusted to pH 9.5. 200 Ml of the mixture was maintained at 30°C for 48 hours.

The mixture was then adjusted to pH 13.5 and extracted with 400 ml ethyl ether. The ether layer was separated, and washed with 100 ml water of pH 2. β-Phenylethylamine hydrochloride precipitated from the water solution and weighed 1.8 g.

EXAMPLE 4

Freeze-dried cells of Micrococcus percitreus AJ 1065 were prepared in the same manner as in Example 1.

Reaction mixtures containing per deciliter, 1 g of one of aromatic amino acids shown in Table 1, 1 g $KH_2PO_4$, 0.01 g pyridoxal phosphate, were 1 g freeze-dried cells, and adjusted to pH 9.5, and 2 ml of each mixture was maintained at 30°C for 48 hours.

Amines in the reaction mixtures were identified by ninhydrin-reagent on paper chromatograms and estimated by extracting the spots on the paper with ethanol.

Table 1

| Aromatic amino acid | Amount of amine formed |
| --- | --- |
| 5-fluoro-DL-tryptophan | + |
| 6-fluoro-DL-tryptophan | + |
| 4-methyl-DL-tryptophan | ++ |
| 5-methyl-DL-tryptophan | ++ |
| 6-methyl-DL-tryptophan | + |
| 7-methyl-DL-tryptophan | + |
| 5-methoxy-DL-tryptophan | + |
| 4-amino-DL-phenylalanine | +++ |
| 4-chloro-DL-phenylalanine | ++ |
| 2-fluoro-DL-phenylalanine | ++ |
| 3-fluoro-DL-phenylalanine | + |
| 4-fluoro-DL-phenylalanine | +++ |
| L-tyrosine | + |
| 3-nitro-DL-tyrosine | +++ |
| 3-iodo-DL-tyrosine | +++ |
| 3,5-diiodo-DL-tyrosine | + |
| 3,5-dibromo-DL-tyrosine | +++ |
| β-phenyl-DL-serine | + |
| 2-hydroxy-DL-phenylalanine | + |

Symbols:
+ OD 0.010 – 0.050
++ OD 0.051 – 0.100
+++ OD 0.101 – 0.200

Ten μl of each reaction mixture was spotted on paper. After developing in the solvent, the paper was treated with ninhydrin and the colored spots were cut out.

After elution with 5 ml ethanol, the OD at 570 nm was estimated.

What is claimes is:

1. A method for producing substituted ethylamine, which comprises holding an amino acid and an effective amount of decarboxylase produced by a Micrococcus in an aqueous solution at pH 5 to 12 at a temperature of 10° to 50°C, and recovering the substituted ethylamine produced from the aqueous solution, said amino acid being tryptophan, 5-hydroxytryptophan, 5-fluorotryptophan, 6-fluorotryptophan, 4-methyltryptophan, 5-methyltryptophan, 6-methyltryptophan, 7methyltryptophan, 5-methoxytryptophan, phenylalanine, β-phenylserine, 2-hydroxyphenylalanine, 4-aminophenylalanine, 4-chlorophenylalanine, 2-fluorophenylalanine, 3-fluorophenylalanine, 4-fluorophenylalanine, tyrosine, 3-nitrotyrosine, 3-iodotyrosine, 3,5-diiodotyrosine, or 3,5-dibromotyrosine, and said substituted ethylamine being tryptamine, serotonin, β-(5-fluoroindolyl) -ethylamine, β-(6-fluoroindolyl) -ethylamine, β-(4-methylindolyl) -ethylamine, β-(5-methylindolyl) -ethylamine, β-(6-methylindolyl) -ethylamine, β-(7-methylindolyl) -ethylamine, β-(5-methoxyindolyl) -ethylamine, β-phenylethylamine, β-phenyl-β-hydroxyethylamine, β-(2-hydroxyphenyl) -ethylamine, β-(4-aminophenyl) -ethylamine, β-(4-chlorophenyl) -ethylamine, β-(2-fluorophenyl) -ethylamine, β-(3-fluorophenyl) -ethylamine, β-(4-fluorophenyl) -ethylamine, β -(4-hydroxyphenyl) -ethylamine, β-(3nitor-4-hydroxyphenyl) -ethylamine, β-(3iodo-4-hydroxyphenyl) -ethylamine, β-(3,5-diiodo-4-hydroxyphenyl) -ethylamine, or β-(3,5-dibromo-4-hydroxyphenyl) -ethylamine.

2. A method as set forth in claim 1, wherein said Micrococcus is Micrcoccous percitreus FERM-P 2200.

3. A method as set forth in claim 1, wherein, said Micrococcus is Micrococcus conglomeratus FERM-P 2199.

* * * * *

UNITED STATES PATENT AND TRADEMARK OFFICE
CERTIFICATE OF CORRECTION

PATENT NO. : 3,930,948
DATED : January 6, 1976
INVENTOR(S) : KONOSUKE SANO ET AL It is certified that error appears in the above-identified patent and that said Letters Patent are hereby corrected as shown below:

Column 6, line 32, change "(3nitor-" to -- (3-nitro- --.

*Signed and Sealed this*

*twenty-third* Day of *March 1976*

[SEAL]

Attest:

RUTH C. MASON
*Attesting Officer*

C. MARSHALL DANN
*Commissioner of Patents and Trademarks*